United States Patent [19]

N'Guyen et al.

[11] Patent Number: 5,023,235

[45] Date of Patent: Jun. 11, 1991

[54] ANTIOXIDANT SYSTEM BASED ON AN ASCORBYL ESTER IN COMBINATION WITH A COMPLEXING AGENT AND A THIOL AND TO COMPOSITIONS CONTAINING THE SAME

[75] Inventors: Quang L. N'Guyen, Antony; Jacqueline Griat, Ablon; Francois Millecamps, Paris, all of France

[73] Assignee: L'Oreal, Paris, France

[21] Appl. No.: 153,450

[22] Filed: Feb. 8, 1988

[30] Foreign Application Priority Data

Feb. 9, 1987 [FR] France ............................. 87 01539

[51] Int. Cl.⁵ ...................... A61K 7/02; A61K 7/021; A61K 7/025; A61K 7/32
[52] U.S. Cl. .................................. 514/18; 252/400.1; 252/400.62; 252/401; 252/402; 252/403; 252/404; 252/405; 252/406; 252/407; 424/59; 424/60; 424/65; 424/76.1; 424/401; 514/12; 530/331
[58] Field of Search ..................... 530/331; 514/18, 12; 252/400.1, 400.6, 401, 402, 403, 404, 405, 406, 407; 424/59, 60, 65, 76.1, 401

[56] References Cited

U.S. PATENT DOCUMENTS 4,898,890  2/1990  Sato et al. ............................ 514/685
4,929,774  5/1990  Fukamachi et al. ................. 568/824

FOREIGN PATENT DOCUMENTS 1239063  4/1967  Fed. Rep. of Germany .
2550648  5/1977  Fed. Rep. of Germany .
1438158  4/1966  France .
2092822  1/1972  France .
2282266  3/1976  France .

Primary Examiner—Lester L. Lee
Attorney, Agent, or Firm—Cushman, Darby & Cushman

[57] ABSTRACT

An antioxidant system comprises at least one ascorbyl ester stabilized with at least one complexing agent and at least one thiol. The antioxidant system is usefully employed in fatty body containing compositions such as cosmetic or alimentary compositions.

16 Claims, 1 Drawing Sheet

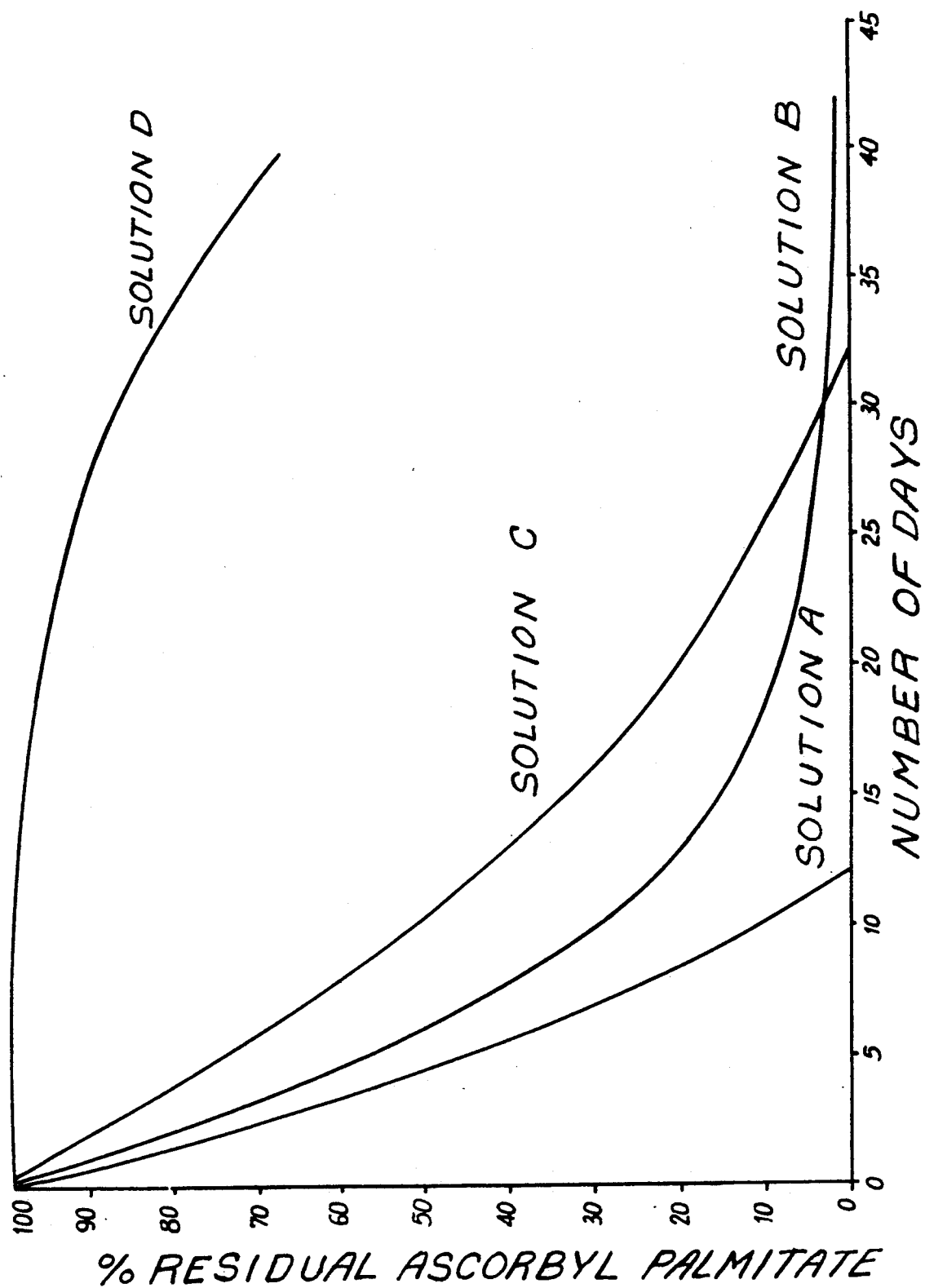

ANTIOXIDANT SYSTEM BASED ON AN ASCORBYL ESTER IN COMBINATION WITH A COMPLEXING AGENT AND A THIOL AND TO COMPOSITIONS CONTAINING THE SAME

The present invention relates to a new antioxidant system based on a stabilized ascorbyl ester containing, in combination, at least one complexing agent and at least one thiol, to the use of such an antioxidant system and to compositions based on oleoginous materials containing such a system and principally to cosmetic compositions.

It is known that fatty bodies have a tendency to oxidize, even at ambient temperature, and that this oxidation (or rancifying) imparts to them new characteristics, principally taste or odor. These characteristics are generally considered undesirable when these fatty bodies are incorporated, for example, in food compositions or in cosmetic compositions.

There is currently employed, in compositions containing fatty bodies, protective agents which, in fact, play the role of antioxidants.

Representative known and currently employed antioxidants include ascorbic acid which acts principally by the direct absorption of oxygen. However, ascorbic acid is only very slightly soluble in fatty bodies and is consequently employed only with difficulty for the protection of fatty bodies against oxidation.

In order to solubilize the ascorbic acid molecule in a fatty material, it has been proposed to use various ascorbyl esters such as, for example, ascorbyl stearate, palmitate or laurate; see for example the article of C.F. Bourgeois, "Revue Francaise des Corps Gras", No. 9, pages 353–356 (September 1981).

It is known that, apart from their own antioxidant properties, ascorbic derivatives also have the characteristic of improving the activity of antioxidant agents such as tocopherols or caffeic acid and its esters, by favoring the regeneration of these antioxidant agents; see for example H.S. Olcott, "Oil Soaps", 18, (1941), 77 and U.S. Pat. No. 2,462,663.

There has also been proposed the use of various improvements of these binary antioxidant agents, of the ascorbic derivative type+tocopherol or ascorbic derivatives+caffeic derivatives, by envisaging the addition of a third constituent, again to improve the antioxidant effects. Representative third constituents of these ternary systems, include principally p-aminobenzoic acid (U.S. Pat. No. 2,462,663), phospholipids (R.W. Riemenschneider et al, "Oil Soap", 1944, 47) and amines (Klaui, "The Functional (Technical) Uses of Vitamins" ed. by M. Stein, University of Nottingham Seminar Vitamins, London, England, 1971, p. 110) etc.

It has now been discovered that it is possible to improve considerably the antioxidant properties of ascorbyl esters by using these antioxidants in conjunction with at least one complexing agent and at least one thiol. A significant synergistic effect is observed.

The present invention thus relates to a new antioxidant system based on at least one stabilized ascorbyl ester, characterized by the fact that it includes at least one complexing agent and at least one thiol in combination therewith.

The ascorbyl ester is certainly an ester which is soluble in the fatty body, and in particular an ester of an aliphatic acid having 6 to 24 carbon atoms, such as, for example, ascorbyl stearate, palmitate or laurate.

By complexing agent is meant a compound which is capable of inhibiting by chelation the catalytic effect of transition metals to the free state in the medium.

Representative useful complexing agents include principally, ethylene diamine tetracetic acid (EDTA), the pentasodim salt of diethylenetriamine pentacetic acid, hexadecylamine salicylate (HDAS), citric acid, tartaric acid and its sodium salt, phytic acid, dibenzyldithiocarbamate, or mixtures thereof.

In addition to at least one of these complexing agents, the composition of the present invention can also contain a secondary complexing agent such as sorbitol.

In accordance with the present invention, by thiol is meant a reducing compound which maintains the ascorbyl esters under their reduced form.

Representative thiols useful in the present invention, include in particular, N-acetyl cysteine, glutathion or a mixture thereof.

The new antioxidant system, such as defined above, can be provided principally in the form of an oily liquid composition; or again the antioxidant system can be provided in the form of an alcoholic solution such as an ethanolic solution.

In the antioxidant system of the present invention, the relative proportions of the three categories of principal constituents depend in particular on the molecular masses of the complexing agent and the thiol. Generally, the thiol is present at a rate of 1 to 37.5 percent and the complexing agent at a rate of 2 to 25 weight percent, relative to the total weight of these three types of constituents.

When a secondary complexing agent is employed at the same time as the principal complexing agent, it is present in an amount such that the mixture is present in an amount between 2 and 25 weight percent.

The ascorbyl ester is generally present in the antioxidant system having three constituents, in an amount between 5 and 87.5 weight percent.

The present invention also relates to an antioxidant system, such as defined above, that also contains another antioxidant selected from tocopherols and caffeic acid (or 3,4-dihydroxycinnamic acid) or its esters.

By "tocopherols" is meant not only α-tocopherol but also β-, γ- or δ-tocopherol as well as mixtures thereof.

Representative esters of caffeic acid include principally the alkyl esters such as the methyl, ethyl or butyl esters and the phytol ester. It has been noted, in a quite surprising manner, that, in such combinations, the antioxidizing activity of the tocopherols and caffeic acid result in a significant synergistic effect because of the presence of the ascorbyl ester stabilized by the complexing agent—thiol couple.

In accordance with this embodiment of the invention, the antioxidant system preferably comprises 0.5 to 20 weight percent tocopherol or caffeic acid (or an ester thereof); 8 to 70 weight percent of a complexing agent; and 2 to 30 weight percent of a thiol.

The molar ratio of the ascorbyl ester to the tocopherol or to caffeic acid or an ester thereof must be preferably greater than or equal to 3.

This synergistic effect can again be improved when the antioxidant system is based on a tocopherol in combination with a polypeptide.

In accordance with this embodiment of the invention, the amount of polypeptide is preferably between 1.5 and 80 weight percent.

The weight ratio of the polypeptide to the tocopherol must be preferably greater than or equal to 3.

The polypeptides have an average molecular weight between about 1,000 and about 100,000. Representative polypeptides include, in particular, the following:

(a) the polypeptide sold under the trade name "KERASOL" by Societe Croda Chemicals Ltd. (polypeptide of soluble keratin having an average molecular weight of about 100,000);

(b) the polypeptide sold under the trade name "Polypeptide SF" by Societe Naarden (polypeptide of partially neutralized animal collagen having an average molecular weight of about 1000);

(c) the polypeptide sold under the trade name "Polypeptide LSN" by Societe Naarden (polypeptide of animal collagen in the form of the ammonium salt containing about 3 percent (max.) of inorganic salt); and (d) the polypeptide sold under the trade name "LACTOLAN" by Laboratories Serobiologiques de Nancy (polypeptide obtained from fresh cow milk previously delipidated).

The present invention also relates to compositions containing fatty bodies characterized by the fact that they include at least one antioxidant system such as defined above.

The compositions of the present invention can be, principally, food compositions (edible oils, lard, butter, margarine or other butter substitutes) or cosmetic compositions.

The fatty bodies present in the cosmetic compositions of the present invention are, for example, fatty bodies of animal origin such as cetin (spermaceti), beeswax, lanolin, perhydrosqualene, turtle oil, etc; vegetable fatty bodies in the form of oils, fats or waxes such as sweet almond oil, avocado oil, olive oil; copra oil or hydrogenated African palm oil, cocoa butter, Carnauba wax, Montan wax; as well as synthetic oils constituted by esters and/or ethers of glycerol or glycol such as, for example, those which are described in French Patent Nos. 75.24656, 75.24657 and 75. 24658.

In addition to more or less oxidizable fatty bodies, the cosmetic composition can contain products sensitive to oxidation such as, for example, vitamin F or β-carotene.

The cosmetic compositions according to the present invention are provided in the form of oily solutions, emulsions, solid products or lotions. They constitute, principally, milks for the care of the skin, creams (face creams, hand creams, body creams, anti-sun creams, make-up remover creams, dye foundation creams), liquid dye foundations, makeup remover milks, anti-sun milks, bath oils, lip rouge, eyelid shadow, deodorant sticks, etc.

In accordance with a preferred embodiment, the cosmetic compositions are provided in the form of creams intended for the protection of skin lipids against oxidation.

In the cosmetic compositions according to the present invention, the antioxidant system, such as defined above, is generally present such that it has the following proportions relative to the total weight of the compositions: tocopherol or caffeic acid (or an ester thereof), 0 to 0.5 percent and preferably, 0.05 to 0.5 percent; ascorbyl ester, 0.45 to 1.6 percent; complexing agent, 0.2 to 0.5 percent; and thiol, 0.1 to 0.7 percent.

When the antioxidant system is based on tocopherol the amount of polypeptide optionally present is between 0.05 to 8 percent relative to the total weight of the composition.

The compositions of the present invention can also contain active components or components conventionally employed in the compositions mentioned above, such as surfactants, dyes, perfumes, astringents, U.V. absorbers, organic solvents, water, etc.

These compositions are prepared in accordance with conventional procedures.

The following nonlimiting examples are given to illustrate several antioxidant systems in accordance with the present invention, as well as cosmetic compositions containing such antioxidant systems.

EXAMPLE 1

| | |
|---|---|
| Ascorbyl palmitate | 76 wt. percent |
| Citric acid | 16 wt. percent |
| N-acetyl cysteine | 8 wt. percent |

EXAMPLE 2

| | |
|---|---|
| Ascorbyl palmitate | 73 wt. percent |
| Citric acid | 9 wt. percent |
| Glutathion | 9 wt. percent |
| N-acetyl cysteine | 9 wt. percent |

EXAMPLE 3

| | |
|---|---|
| Ascorbyl palmitate | 79 wt. percent |
| Citric acid | 5 wt. percent |
| EDTA | 12 wt. percent |
| N-acetyl cysteine | 4 wt. percent |

EXAMPLE 4

| | |
|---|---|
| Tocopherols (mixture of α−, β−, γ− and δ-tocopherols) | 7 wt. percent |
| Ascorbyl palmitate | 65 wt. percent |
| Citric acid | 7 wt. percent |
| EDTA | 13 wt. percent |
| N-acetyl cysteine | 8 wt. percent |

EXAMPLE 5

| | |
|---|---|
| Tocopherols | 11 wt. percent |
| Ascorbyl palmitate | 65 wt. percent |
| Hexadecylamine salicylate | 6 wt. percent |
| Sorbitol | 9 wt. percent |
| N-acetyl cysteine | 9 wt. percent |

EXAMPLE 6

| | |
|---|---|
| Tocopherols | 16 wt. percent |
| Ascorbyl palmitate | 63 wt. percent |
| Glutathion | 6 wt. percent |
| N-acetyl cysteine | 3 wt. percent |
| Citric acid | 3 wt. percent |
| EDTA | 9 wt. percent |

EXAMPLE 7

| | |
|---|---|
| Caffeic acid | 8 wt. percent |
| Ascorbyl palmitate | 49 wt. percent |
| Citric acid | 4 wt. percent |
| EDTA | 10 wt. percent |
| Glutathion | 10 wt. percent |

| N-acetyl cysteine | 19 wt. percent |

EXAMPLE 8

| Caffeic acid | 7 wt. percent |
| Ascorbyl palmitate | 65 wt. percent |
| Sodium tartrate | 8 wt. percent |
| N-acetyl cysteine | 20 wt. percent |

EXAMPLE 9

| Caffeic acid | 8 wt. percent |
| Ascorbyl palmitate | 70 wt. percent |
| Hexadecylamine salicylate | 15 wt. percent |
| N-acetyl cysteine | 7 wt. percent |

EXAMPLE 10

| Tocopherols | 9 wt. percent |
| Ascorbyl palmitate | 36 wt. percent |
| Citric acid | 4.5 wt. percent |
| N-acetyl cysteine | 4.5 wt. percent |
| EDTA | 1.5 wt. percent |
| "KERASOL", polypeptide (active material) | 44.5 wt. percent |

EXAMPLE 11

| Tocopherols | 5 wt. percent |
| Ascorbyl palmitate | 21.5 wt. percent |
| Citric acid | 2.5 wt. percent |
| N-acetyl cysteine | 1 wt. percent |
| Glutathion | 1 wt. percent |
| EDTA | 2.5 wt. percent |
| "Polypeptide SF", polypeptide (active material) | 66.5 wt. percent |

Examples of Cosmetic Compositions
Example I - Skin cream (water-in-oil emulsion)

| Magnesium lanolate | 14.4 wt. percent |
| Lanolin alcohol | 3.6 wt. percent |
| Turnsole oil | 40.0 wt. percent |
| Isopropyl myristate | 8.0 wt. percent |
| Ozokerite | 4.0 wt. percent |
| Vitamin F | 2.0 wt. percent |
| Ascorbic acid | 0.5 wt. percent |
| Soy lecithin | 5.0 wt. percent |
| Tocopherols | 0.25 wt. percent |
| Ascorbyl palmitate | 1.0 wt. percent |
| Glutathion | 0.1 wt. percent |
| N-acetyl cysteine | 0.05 wt. percent |
| Citric acid | 0.05 wt. percent |
| EDTA | 0.15 wt. percent |
| Perfume | 0.8 wt. percent |
| Methyl parahydroxybenzoate | 0.3 wt. percent |
| Water, sufficent amount for | 100 wt. percent |

Example II - Anhydrous Balm

| Karite oil | 60.0 wt. percent |
| Turnsole oil | 20.0 wt. percent |
| Vitamin F | 2.0 wt. percent |
| Soy lecithin | 4.9 wt. percent |
| Tocopherols | 0.2 wt. percent |

Example II - Anhydrous Balm (continued)

| Ascorbyl palmitate | 1.13 wt. percent |
| Glutathion | 0.35 wt. percent |
| Citric acid | 0.15 wt. percent |
| N-acetyl cysteine | 0.35 wt. percent |
| EDTA | 0.15 wt. percent |
| Petrolatum, sufficient amount for | 100 wt. percent |

Example III - Face and body oil

| Karite oil | 2.0 wt. percent |
| Turnsole oil | 31.8 wt. percent |
| Vitamin F | 2.0 wt. percent |
| Soy oil | 32.0 wt. percent |
| Tocopherols | 0.1 wt. percent |
| Citric acid | 0.05 wt. percent |
| Ascorbyl palmitate | 1.0 wt. percent |
| N-acetyl cysteine | 0.1 wt. percent |
| EDTA | 0.15 wt. percent |
| Soy lecithin | 0.1 wt. percent |
| Peanut oil, sufficient amount for | 100 wt. percent |

Example IV - Skin care cream (oil-in-water emulsion)

| Sorbitan monostearate having 20 moles of ethylene oxide ("Tween 60") | 1.0 wt. percent |
| Glycerol stearate | 2.0 wt. percent |
| Stearic acid | 1.4 wt. percent |
| Triethanolamine | 0.7 wt. percent |
| Cetyl alcohol | 0.5 wt. percent |
| Turnsole oil | 15.0 wt. percent |
| Vitamin F | 2.0 wt. percent |
| Ascorbic acid | 1.0 wt. percent |
| Soy lecithin | 0.6 wt. percent |
| Petrolatum oil | 2.4 wt. percent |
| Caffeic acid | 0.2 wt. percent |
| Ascorbyl palmitate | 1.5 wt. percent |
| Hexadecylamine salicylate | 0.5 wt. percent |
| N-acetyl cysteine | 0.3 wt. percent |
| Carboxy vinyl polymer, sold under the name "Carbopol 940" by Goodrich | 0.2 wt. percent |
| Triethanolamine | 0.2 wt. percent |
| Perfume | 0.8 wt. percent |
| Preservative (methyl parahydroxybenzoate) | 0.25 wt. percent |
| Water, sufficient amount for | 100 wt. percent |

Example V - Body care fluid

1st phase

| Non-ionic amphiphilic lipid having the formula, | 4.5 wt. percent |

$$R-(OCH_2-CH)_n-OH,$$
$$\phantom{R-(OCH_2-}|$$
$$\phantom{R-(OCH_2-}CH_2OH$$

wherein R is a hexadecyl radical and n has a statistic average value equal to 3

| Cholesterol | 4.5 wt. percent |
| Dicetylphosphate | 1.0 wt. percent |
| Methyl parahydroxybenzoate | 0.3 wt. percent |
| Sterile demineralized water | 30.0 wt. percent |

2nd phase
To the dispersion of spherules obtained in the first phase, the following components are added.

| Perfume | 0.4 wt. percent |
| Turnsole oil | 10.0 wt. percent |
| Paraffin oil | 4.0 wt. percent |
| Vitamin F | 2.0 wt. percent |
| Soy lecithin | 1.0 wt. percent |
| Caffeic acid | 0.1 wt. percent |
| Ascorbyl palmitate | 1.0 wt. percent |

| Example V - Body care fluid | |
|---|---|
| Hexadecylamine salicylate | 0.2 wt. percent |
| N-acetyl cysteine | 0.1 wt. percent |
| Carboxy vinyl polymer, sold under the name "Carbopol 940" by Goodrich | 0.4 wt. percent |
| Triethanolamine | 0.4 wt. percent |
| Demineralized water, sufficient amount for | 100 wt. percent |

| Example VI - Solar cream | |
|---|---|
| Magnesium lanolate | 7.2 wt. percent |
| Lanolin alcohol | 1.8 wt. percent |
| Turnsole oil | 20.6 wt. percent |
| Vitamin F | 2.0 wt. percent |
| β-carotene | 0.1 wt. percent |
| Soy lecithin | 0.4 wt. percent |
| Paraffin oil | 4.0 wt. percent |
| Caffeic acid | 0.1 wt. percent |
| Ascorbyl palmitate | 0.4 wt. percent |
| Citric acid | 0.05 wt. percent |
| Glutathion | 0.05 wt. percent |
| N-acetyl cysteine | 0.05 wt. percent |
| EDTA | 0.15 wt. percent |
| Ascorbic acid | 1.0 wt. percent |
| Polyethylene powder | 10.0 wt. percent |
| 2-phenyl-5-benzimidazole sulfonic acid, sold under the name "EUSOLEA 232" by Merck | 3.0 wt. percent |
| 2-hydroxy-4-methoxy benzophenone, sold under the name "UVINUL M40" by BASF | 3.0 wt. percent |
| Perfume | 1.0 wt. percent |
| Methyl parahydroxybenzoate | 0.15 wt. percent |
| Propyl parahydroxybenzoate | 0.15 wt. percent |
| Water, sufficient amount for | 100 wt. percent |

| Example VII - Face and body oil | |
|---|---|
| Karite oil | 2.0 wt. percent |
| Turnsole oil | 31.8 wt. percent |
| Vitamin F | 2.0 wt. percent |
| Soy oil | 32.0 wt. percent |
| Tocopherols | 0.3 wt. percent |
| Citric acid | 0.15 wt. percent |
| Ascorbyl palmitate | 1.2 wt. percent |
| N-acetyl cysteine | 0.15 wt. percent |
| EDTA | 0.05 wt. percent |
| "KERASOL", polypeptide (active material) | 1.5 wt. percent |
| Soy lecithin | 0.1 wt. percent |
| Peanut oil, sufficient amount for | 100 wt. percent |

| Example VIII - Skin care cream (water-in-oil emulsion) | |
|---|---|
| Magnesium lanolate | 14.4 wt. percent |
| Lanolin alcohol | 3.6 wt. percent |
| Turnsole oil | 40.0 wt. percent |
| Isopropyl myristate | 8.0 wt. percent |
| Ozokerite | 4.0 wt. percent |
| Vitamin F | 2.0 wt. percent |
| Ascorbic acid | 0.6 wt. percent |
| Soy lecithin | 5.0 wt. percent |
| Tocopherols | 0.2 wt. percent |
| Ascorbyl palmitate | 0.9 wt. percent |
| Glutathion | 0.05 wt. percent |
| N-acetyl cysteine | 0.05 wt. percent |
| Citric acid | 0.1 wt. percent |
| EDTA | 0.1 wt. percent |
| "Polypeptide SF", polypeptide (active material) | 2.8 wt. percent |
| Perfume | 0.8 wt. percent |
| Methyl parahydroxybenzoate | 0.3 wt. percent |
| Water, sufficent amount for | 100 wt. percent |

1. Stabilization study of ascorbyl palmitate

In order to determine the stabilization effect of the complexing agent—thiol couple on ascorbyl palmitate, several solutions in ethanol have been studied.

The determination, over time, of the amount of degradation of ascorbyl plamitate has been effected by HPLC.

The solutions studied were the following:
Solution A—Ascorbyl palmitate, 0.05 wt. percent;
Solution B—Ascorbyl palmitate, 0.05 wt. percent, N-acetyl cysteine, 0.01 ;
Solution C—Ascorbyl palmitate, 0.05 wt. percent EDTA, 0.01
Solution D—Ascorbyl palmitate, 0.05 wt. percent N-acetyl cysteine, 0.01 EDTA, 0.01

The results obtained are shown on FIG. 1.

As can be noted, as a function of the curve corresponding to Solution D, the amount of degradation of ascorbyl palmitate is considerably lower than the other solutions which demonstrates the stabilizing character of the complexing agent (EDTA)—thiol (N-acetyl cysteine) couple.

In effect, at the end of 40 days, the amount of degradation of ascorbyl palmitate in Solution D is only about 30 percent whereas for Solutions A, B and C, the ascorbyl palmitate is completely degraded at the end of the same time period.

2. Study of the synergism effect between ascorbyl palmitate, stabilized by a mixture of HDAS+N-acetyl cysteine, and tocopherols The oil employed in this study is vitamin F.

Mixtures of vitamin F with various amounts of tocopherols, ascorbyl palmitate, hexadecylamine salicylate (HDAS) and N-acetyl cysteine have been prepared. The amounts of each component are set forth in Table I below; they are expressed in percent and are relative to the same amount (100 g) of vitamin F.

Each sample being studied is heated to 100° C. under a bubbling of air (20 l/hr) so as to effect accelerated oxidation of the oil.

The concentration of volatile acids, resulting from the degradation of the hydroperoxides and aldehydes, formed by oxidation, is continuously followed in a cell filled with water into which is inserted a platinum electrode. This electrode measures the evolution of the conductivity as a function of time. Oxidation causes an increase in the conductivity.

The induction time, which represents the time at the end of which oxidation begins, is determined by the intersection of the two tangents at the self-oxidation curve.

TABLE I

| Ascorbyl palmitate | HDAS* | N-acetyl cysteine | Tocopherols | Induction Time |
|---|---|---|---|---|
| — | — | — | 0.20 | 60 min. |
| 0.20 | — | — | — | 20 min. |
| 0.20 | — | — | 0.20 | 92 min. |
| — | 0.20 | 0.10 | — | 15 min |
| 0.20 | 0.20 | — | 0.20 | 93 min. |
| 0.20 | — | 0.10 | 0.20 | 96 min. |

TABLE I-continued

| Ascorbyl palmitate | HDAS* | N-acetyl cysteine | Tocopherols | Induction Time |
|---|---|---|---|---|
| 0.20 | 0.20 | 0.10 | 0.20 | 114 min. |

*hexadecylamine salicylate

The induction time of vitamin F, alone, without an antioxidant is 15 minutes.

Table I shows that the combination of hexadecylamine salicylate and N-acetyl cysteine, alone produces no effect. On the other hand, as is known, the combination of α-tocopherol and ascorbyl palmitate leads to a significant increase in the induction time. This induction time is again significantly improved by the combination of hexadecylamine salicylate+N-acetyl cysteine although each of these two agents added alone to an α-tocopherol+ascorbyl palmitate mixture is practically without influence.

3. Study of the synergism effect between ascorbyl palmitate, stabilized by a mixture of HDAS+N-acetyl cysteine and caffeic acid The procedures set forth in part 2, above, are repeated. The results are given in Table II, below.

TABLE II

| Ascorbyl palmitate | HDAS | N-acetyl cysteine | Caffeic Acid | Induction Time |
|---|---|---|---|---|
| 0.25 | — | — | 0.10 | 93 min. |
| 0.21 | 0.21 | 0.10 | 0.10 | 315 min. |

Table II shows the synergism effect achieved by the addition, to the system studied, of the combination of hexadecylamine salicylate - N-acetyl cysteine.

This combination considerably increases the induction time of the caffeic acid+ascorbyl palmitate system, although used alone, this combination, as has been shown in Table I, above, has no effect.

What is claimed is:

1. An antioxidant system comprising from 5 to 87.5 weight percent of an ascorbyl ester of an aliphatic acid having 6 to 24 carbon atoms stabilized with (i) a complexing agent in an amount ranging from 2 to 25 weight percent selected from the group consisting of ethylenediamine tetracetic acid, pentasodium salt of diethylenetriamine pentacetic acid, hexadecylamine salicylate, citric acid, tartaric acid, sodium-tartarate, phytic acid, dibenzyldithiocarbamate and mixtures thereof, and (ii) a thiol in an amount ranging from 1 to 37.5 weight percent selected from the group consisting of N-acetyl cysteine, glutathione and mixtures thereof, said percentages being based on the total weight of said system.

2. The antioxidant system of claim 1 wherein said ascorbyl ester is selected from the group consisting of ascorbyl stearate, ascorbyl palmitate and ascorbyl laurate.

3. The antioxidant system of claim 3 which also contains sorbitol as a secondary complexing agent.

4. A cosmetic composition comprising a cosmetically acceptable fatty body and an antioxidant system comprising:
   (a) a tocopherol, caffeic acid, or caffeic acid ester present in an amount ranging from 0 to 0.5 percent by weight based on the total weight of said composition,
   (b) an ascorbyl ester of an aliphatic acid having 6 to 24 carbon atoms present in an amount ranging from 0.45 to 1.6 percent by weight based on the total weight of said composition,
   (c) a complexing agent in an amount ranging from 0.2 to 0.5 percent by weight based on the total weight of said composition, said complexing agent being selected from the group consisting of ethylenediamine tetracetic acid, pentasodium salt of diethylenetriamine pentacetic acid, hexadecylamine salicylate, citric acid, tartaric acid, sodium tartrate, phytic acid, dibenzyldithiocarbamate and mixtures thereof, and
   (d) a thiol present in an amount ranging from 0.1 to 0.7 percent by weight based on the total weight of said composition, said thiol being selected from the group consisting of N-acetyl cysteine, glutathione and mixtures thereof.

5. The antioxidant system of claim 1 which also includes at least one tocopherol or a mixture of tocopherol.

6. The antioxidant system of claim 5 which also includes a polypeptide having an average molecular weight between 1,000 and 100,000, the weight ratio of said polypeptide to tocopherol being greater than or equal to 3.

7. The antioxidant system of claim 1 which also contains caffeic acid or an ester thereof.

8. The antioxidant system of claim 1 which comprises:
   (a) 0 to 20 weight percent of a tocopherol, caffeic acid or caffeic acid ester,
   (b) 8 to 70 weight percent of said ascorbyl ester,
   (c) 4 to 20 weight percent of said complexing agent, and
   (d) 2 to 30 weight percent of said thiol.

9. The antioxidant system of claim 1 which comprises:
   (a) 0.5 to 20 weight percent of a tocopherol,
   (b) 8 to 70 weight percent of said ascorbyl ester,
   (c) 4 to 20 weight percent of said complexing agent,
   (d) 2 to 30 weight percent of said thiol, said antioxidant system also containing
   (e) 1.5 to 80 weight percent of a polypeptide having an average molecular weight between 1,000 and 100,000, the weight ratio of aid polypeptide to said tocopherol being greater than or equal to 1.

10. The antioxidant system of claim 5 wherein the molar ratio of ascorbyl ester to said tocopherol is greater than or equal to 3.

11. The antioxidant system of claim 7 wherein the molar ratio of ascorbyl ester to said caffeic acid or an ester thereof is greater than or equal to 3.

12. The cosmetic composition of claim 4 wherein said tocopherol, caffeic acid or caffeic acid ester is present in an amount ranging from 0.05 to 0.5 percent by weight based on the total weight of said composition.

13. The cosmetic composition of claim 4 wherein said oxidant system comprises:
   (a) a tocopherol present in an amount ranging from 0.05 to 0.5 weight percent,
   (b) said ascorbyl ester present in an amount ranging from 0.45 to 1.6 weight percent,
   (c) said complexing agent present in an amount ranging from 0.2 to 0.5 weight percent, and
   (d) said thiol present in an amount ranging from 0.1 to 0.7 weight percent,
   said composition also including a polypeptide having an average molecular weight between 1,000 and 100,000 present in an amount ranging from 0.05 to 8 percent by weight based on the total weight of said composition.

14. The cosmetic composition of claim 4 wherein said ascorbyl ester is ascorbyl palmitate.

15. The cosmetic composition of claim 4 in the form of a cream to protect against the oxidation of skin lipids.

16. The antioxidant system of claim 1 wherein said ascoryl ester is ascorbyl palmitate stabilized with ethylenediamine tetracetic acid as a complexing agent and said thio is N-acetyl cysteine.

* * * * *